United States Patent [19]

Krüger et al.

[11] Patent Number: 4,678,777
[45] Date of Patent: Jul. 7, 1987

[54] PEST-COMBATING AGENTS CONTAINING PHOSPHORUS-HETEROCYCLIC COMPOUNDS

[75] Inventors: Bernd-Wieland Krüger; Hellmut Hoffmann, both of Wuppertal; Ernst Roos, Odenthal; Wolfgang Behrenz, Overath, all of Fed. Rep. of Germany

[73] Assignee: Bayer Aktiengesellschaft, Leverkusen, Fed. Rep. of Germany

[21] Appl. No.: 762,979

[22] Filed: Aug. 6, 1985

[30] Foreign Application Priority Data

Aug. 24, 1984 [DE] Fed. Rep. of Germany ....... 3431256

[51] Int. Cl.⁴ ............................................ A01N 57/36
[52] U.S. Cl. .................................................. 514/110
[58] Field of Search ................................. 514/110, 111

[56] References Cited

U.S. PATENT DOCUMENTS

| | | | |
|---|---|---|---|
| 3,006,947 | 10/1961 | Lanham | 260/461 |
| 3,192,162 | 6/1965 | Bartlett et al. | 252/46.6 |
| 3,270,093 | 8/1966 | Gradsten | 260/937 |
| 3,740,427 | 6/1973 | Hoffmann et al. | 514/110 |
| 4,016,265 | 4/1977 | Inoue et al. | 424/115 |
| 4,257,987 | 3/1981 | Arend et al. | 558/136 |

FOREIGN PATENT DOCUMENTS

| | | | |
|---|---|---|---|
| 0029138 | 5/1981 | European Pat. Off. | |
| 2244090 | 3/1974 | Fed. Rep. of Germany | |
| 4114119 | 8/1966 | Japan | 514/111 |
| 4512299 | 5/1970 | Japan | 514/111 |

OTHER PUBLICATIONS

Poole et al, "Determination of Bifunctional Compounds", VII, Ethylphosphonothioic Dichloride . . . , Journal of Chromatography, vol. 178, No. 1, (1979), pp. 496–503.

*Primary Examiner*—Allen J. Robinson
*Attorney, Agent, or Firm*—Sprung Horn Kramer & Woods

[57] ABSTRACT

An arthropodicidal composition comprising an arthropodicidally effective amount of an arthropodicidally active compound and a synergistically effective amount of at least one compound of the formula

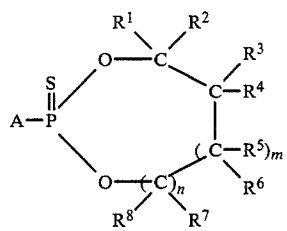

in which
A is amino, alkylamino, dialkylamino or N-alkyl-N-arylamino, or an optionally substituted alkyl, alkenyl, alkoxy, alkenyloxy, alkylthio, aralkyl, aralkoxy, phenyl, phenoxy or phenylthio radical,
$R^1$, $R^2$, $R^3$, $R^4$, $R^5$, $R^6$, $R^7$ and $R^8$ each independently is hydrogen, or an optionally halogen-substituted alkyl, alkenyl, alkoxyalkyl or alkylthioalkyl radical, or is halogen, nitro or dialkylaminoalkyl, or is optionally substituted phenyl or benzyl, or two of the radicals $R^1$ to $R^8$, together with the carbon atom or atoms to which they are bonded form an optionally substituted monocyclic or bicyclic ring and
n and m each independently is 0 or 1.

10 Claims, No Drawings

PEST-COMBATING AGENTS CONTAINING PHOSPHORUS-HETEROCYCLIC COMPOUNDS

The present invention relates to pest-combating agents containing phosphorus-heterocyclic compounds, preferably for combating arthropods, in particular insects, mites and arachnids.

Synergistic mixtures of insecticidal active compounds, for example of pyrethroids with certain methylenedioxyphenyl derivatives, for example piperonyl butoxide, as synergists have already been disclosed (compare, for example, K. Naumann, Chemie der Pflanzenschutz- und Schädlingsbekämpfungsmittel (Chemistry of Plant Protection and Pest-combating Agents), Springer Verlag Berlin, Volume 7 (1981) pages 3–6). However, the activity of these agents is not always completely satisfactory under the conditions which arise in practice.

It has now been found that the phosphorus-heterocyclic compounds of the general formula I

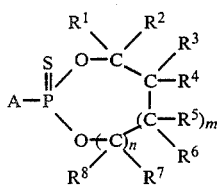
(I)

in which
A represents amino, alkylamino, dialkylamino or N-alkyl-N-arylamino, or represents optionally substituted radicals from the series comprising alkyl, alkenyl, alkoxy, alkenyloxy, alkylthio, aralkyl, aralkoxy, phenyl, phenoxy and phenylthio,
$R^1$, $R^2$, $R^3$, $R^4$, $R^5$, $R^6$, $R^7$ and $R^8$ are identical or different and represent hydrogen, or represent optionally halogen-substituted radicals from the series comprising alkyl, alkenyl, alkoxyalkyl and alkylthioalkyl, or represent halogen, nitro or dialkylaminoalkyl, or represent phenyl or benzyl, each of which is optionally substituted,
and wherein
two of the radicals $R^1$ to $R^8$, together with the carbon atom or atoms to which they are bonded, can also form an optionally substituted monocyclic or bicyclic ring and
n and m are identical or different and denote 0 or 1, when mixed with active compounds which are active against arthropods, preferably with insecticides and acaricides, display very good synergistic properties which enable them to be used in pest-combating agents.

The present invention thus relates to the use of the phosphorus-heterocyclic compounds of the general formula I as synergists for improving the action of arthropodicides, in particular insecticides and acaricides.

The present invention furthermore relates to new pest-combating agents which contain the phosphorus-heterocyclic compounds of the general formula I as synergists, in addition to arthropodicidal, in particular insecticidal and acaricidal, active compounds.

Possible arthropodicides (substances which are active against arthropods) are virtually all the customary active compounds (compare, for example, K. H. Büchel, Pflanzenschutz und Schädlingsbekämpfungsmittel (Plant Protection and Pest-combating Agents), Thieme Verlag Stuttgart, 1977, and Farm Chemicals Handbook 1979, Meister Publishing Co., Willougby, 1979).

The compounds of the formula I contain several chirality centers and exist in the form of optically pure diastereomers or in the form of diastereomer mixtures.

Preferably, the phosphorus-heterocyclic compounds of the general formula (I) are used together with arthropodicidal
1. carbamic acid esters and/or
2. carboxylic acid esters, including the naturally occurring and synthetic pyrethroids, and/or
3. phosphorus compounds, such as phosphoric acid esters and phosphonic acid esters, including the thio and dithio compounds.

Surprisingly, the action of the new active compound combinations according to the invention against arthropods is substantially more powerful than the action of the individual components or the sum of the actions of the individual components. It is furthermore considerably more powerful than the action of active compound combinations with the known commercially available synergist piperonyl butoxide. The phosphorus-heterocyclic compounds which can be used according to the invention also exhibit excellent synergistic activities not only with one class of active compound but with active compounds from the most diverse groups of chemical substances.

The synergistic action of the compounds of the general formula (I) particularly preferentially manifests itself with
(1) carbamic acid esters of the formula (II)

(II)

in which
$R^9$ represents an optionally substituted carbocyclic or heterocyclic aromatic radical or represents an optionally substituted oxime radical (the radicals $R^9$ described below being preferred),
$R^{10}$ represents $C_1$–$C_4$-alkyl and
$R^{11}$ represents hydrogen or $C_1$–$C_4$-alkyl, or represents a radical Y,
wherein
Y represents the radical —CO—$R^{12}$,
wherein
$R^{12}$ represents halogen, $C_1$–$C_4$-alkyl, $C_1$–$C_4$-alkoxy, $C_3$–$C_5$-alkenoxy, $C_3$–$C_5$-alkinoxy, $C_1$–$C_4$-alkylthio, $C_1$–$C_4$-alkyl-amino, di-$C_1$–$C_4$-alkylamino or $C_1$–$C_4$-alkyl-hydroxylamino, or represents phenoxy, phenylthio or phenylamino, each of which is optionally substituted by halogen, nitro, cyano, trifluoromethyl, $C_1$–$C_4$-alkyl, $C_1$–$C_4$-alkoxy, $C_1$–$C_4$-alkylenedioxy, $C_1$–$C_4$-alkylthio or $C_1$–$C_4$-alkoxy-carbonyl, or represents 2,3-dihydro-2,2-dimethyl-7-benzofuranyl, or represents the radical

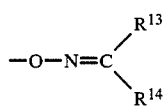

wherein
$R^{13}$ represents hydrogen, $C_1$–$C_4$-alkyl or di-$C_1$–$C_4$-alkylamino-carbonyl and $R^{14}$ represents $C_1$–$C_4$-alkyl, $C_1$–$C_4$-alkylthio, cyano-$C_1$–$C_4$-alkylthio or $C_1$–$C_4$-alkylthio-$C_1$–$C_4$-alkyl, or the two radicals $R^{13}$ and $R^{14}$ together represent $C_2$–$C_8$-alkanediyl, which is optionally interrupted by oxygen, sulphur, SO or $SO_2$, or in which Y represents the radical $-S_o(O)_p-R^{15}$, wherein o represents 1 or 2, p represents 0, 1 or 2 and $R^{15}$ represents optionally halogen-substituted $C_1$–$C_4$-alkyl, $C_3$–$C_5$-alkenyl, $C_3$–$C_5$-alkinyl or $C_3$–$C_6$-cycloalkyl, or represents phenyl, benzyl or phenethyl, each of which is optionally substituted by halogen, cyano, nitro, trifluoromethyl, trifluoromethoxy, trifluoromethylthio, $C_1$–$C_4$-alkyl or $C_1$–$C_4$-alkoxy, or represents the radical

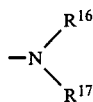

wherein $R^{16}$ represents $C_1$–$C_4$-alkyl, $C_3$–$C_5$-alkenyl, $C_3$–$C_5$-alkinyl, $C_3$–$C_6$-cycloalkyl or benzyl and $R^{17}$ represents $C_1$–$C_4$-alkyl, $C_3$–$C_5$-alkenyl, $C_3$–$C_5$-alkinyl, $C_3$–$C_6$-cycloalkyl, benzyl, phenethyl, halogenocarbonyl, formyl, $C_1$–$C_4$-alkylcarbonyl, $C_1$–$C_4$-alkoxy-carbonyl, $C_1$–$C_4$-alkoxyphenoxy-carbonyl, $C_3$–$C_5$-alkinoxy-carbonyl, $C_3$–$C_5$-alkenoxycarbonyl, $C_1$–$C_4$-alkylthiocarbonyl, $C_1$–$C_4$-alkyl-aminocarbonyl, $C_1$–$C_4$-alkyl-hydroxylamino-carbonyl, $C_1$–$C_{10}$-alkylphenoxycarbonyl, di-$C_1$–$C_4$-alkyl-aminocarbonyl, phenylthiocarbonyl, phenoxycarbonyl or 2,3-dihydro-2,2-dimethyl-7-benzofuranyloxycarbonyl, or represents phenylsulphenyl, phenylsulphinyl, phenylsulphonyl or phenyl, each of which is optionally substituted by halogen, cyano, nitro, trifluoromethyl, $C_1$–$C_{10}$-alkyl or $C_1$–$C_4$-alkoxy, or represents the radical

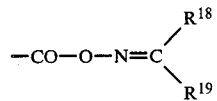

wherein $R^{18}$ has the meaning given above for $R^{13}$ and $R^{19}$ has the meaning given above for $R^{14}$, and wherein, furthermore, in the radical

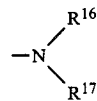

the radicals $R^{16}$ and $R^{17}$ together represent a hydrocarbon chain which has 3 to 8 carbon atoms and is optionally interrupted by oxygen or sulphur, and wherein, furthermore, $R^{15}$ can also represent the same radical to which the radical $-S_o(O)_p-R^{15}$ is bonded.

Very particularly preferred active compound components are carbamic acid esters of the formula (II) in which $R^9$ represents radicals from the series comprising phenyl, naphthyl, 2,3-dihydro-7-benzofuranyl, pyrazolyl and pyrimidinyl, each of which is optionally substituted by $C_1$–$C_4$-alkyl, $C_2$–$C_4$-alkenyl, $C_1$–$C_4$-alkoxy, $C_1$–$C_4$-alkoxy-methyl, $C_1$–$C_4$-alkylthio, $C_1$–$C_4$-alkylthio-methyl, $C_1$–$C_4$-alkylamino, di-($C_1$–$C_4$-alkyl)-amino, di-($C_3$–$C_4$-alkenyl)-amino, halogen, dioxolanyl, methylenedioxy and/or the radical $-N=CH-N(CH_3)_2$, or in which $R^9$ represents an alkylideneamino radical of the formula

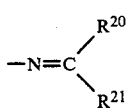

in which $R^{20}$ and $R^{21}$ have the meaning given above for $R^{13}$ and, respectively, $R^{14}$, and $R^{10}$ represents $C_{1-4}$-alkyl and $R^{11}$ represents hydrogen or $C_1$–$C_4$-alkyl (preferably hydrogen).

The following N-methylcarbamic acid esters may be mentioned as examples of the carbamic acid esters of the formula (II): the 2-methyl-phenyl, 2-ethyl-phenyl, 2-isopropyl-phenyl, 2-sec.-butyl-phenyl, 2-methoxy-phenyl, 2-ethoxy-phenyl, 2-iso-propoxy-phenyl, 4-methyl-phenyl, 4-ethyl-phenyl, 4-n-propyl-phenyl, 4-methoxy-phenyl, 4-ethoxy-phenyl, 4-n-propoxy-phenyl, 3,4,5-trimethyl-phenyl, 3,5-dimethyl-4-methylthio-phenyl, 3-methyl-4-dimethylaminophenyl, 2-ethylthiomethyl-phenyl, 1-naphthyl, 2,3-dihydro-2,2-dimethyl-7-benzofuranyl, 2,3-(dimethylmethylenedioxy)-phenyl, 2-(4,5-dimethyl-1,3-dioxolan-2-yl)-phenyl, 1-methylthioethylidene-amino, 2-methylthio-2-methylpropylideneamino, 1-(2-cyano-ethylthio)-ethylideneamino and 1-methylthiomethyl-2,2-dimethylpropylideneamino ester of N-methyl-carbamic acid.

The synergistic action of the compounds of the general formula (I) furthermore preferentially manifests itself with (2) carboxylic acid esters of the formula (III)

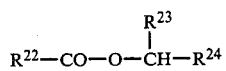

(III)

in which $R^{22}$ represents an open-chain or cyclic alkyl radical, which is optionally substituted by halogen, alkyl or cycloalkyl, or by alkenyl which is optionally substituted by halogen, alkyl and/or alkoxy, or by phenyl or by styryl, each of which is optionally substituted by halogen or optionally halogen-substituted radicals from the series comprising alkyl, alkoxy, alkylenedioxy and/or alkylthio, or by spirocyclically linked optionally halogen-substituted cycloalk(en)yl, which is optionally benzofused, and in which, furthermore, $R^{23}$ represents hydrogen, alkyl, halogenoalkyl, alkenyl, alkinyl or cyano and $R^{24}$ represents an optionally substituted alkyl or aryl radical or represents a heterocyclic radical, or, together with $R^{23}$ and the carbon atom to which the two radicals are bonded, forms a cyclopentenone ring.

Very particularly preferred active compound components are carboxylic acid esters of the formula (III) in which $R^{22}$ (a) represents the radical

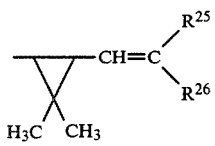

wherein $R^{25}$ represents hydrogen, methyl, fluorine, chlorine or bromine and $R^{26}$ represents methyl, fluorine, chlorine, bromine, $C_1$-$C_2$-fluoroalkyl or $C_1$-$C_2$-chlorofluoroalkyl, or represents phenyl which is optionally substituted by halogen and/or optionally halogen-substituted radicals from the series comprising $C_1$-$C_4$-alkyl, $C_1$-$C_4$-alkoxy, $C_1$-$C_4$-alkylthio and/or $C_1$-$C_2$-alkylenedioxy, or wherein the two radicals $R^{25}$ and $R^{26}$ represent $C_2$-$C_5$-alkanediyl (alkylene);

or in which $R^{22}$ (b) represents the radical

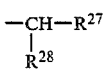

wherein $R^{27}$ represents phenyl which is optionally substituted by halogen and/or by optionally halogen-substituted radicals from the series comprising $C_1$-$C_4$-alkyl, $C_1$-$C_4$-alkoxy, $C_1$-$C_4$-alkylthio and $C_1$-$C_2$-alkylenedioxy and $R^{28}$ represents isopropyl or cyclopropyl; or in which $R^{22}$ (c) represents methyl or one of the radicals

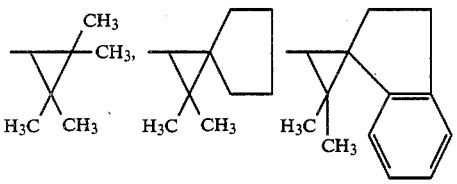

the dotted lines being intended to indicate possible double bonds, and in which $R^{23}$ represents hydrogen, $C_1$-$C_4$-alkyl, $C_1$-$C_4$-halogenoalkyl, cyano or ethinyl and $R^{24}$ represents the radicals from the series comprising phenyl, furyl and tetrahydrophthalimido, it being possible for these radicals to be substituted by halogen and/or radicals from the series comprising $C_1$-$C_4$-alkyl, $C_2$-$C_4$-alkenyl, $C_1$-$C_4$-alkoxy, $C_2$-$C_4$-alkenoxy, $C_1$-$C_4$-alkylthio, $C_1$-$C_2$-alkylenedioxy, phenoxy and/or benzyl, which can in turn be substituted by halogen, and wherein $R^{24}$ preferably represents pentafluorophenyl, 3,4-dichlorophenyl or tetrahydrophthalimido, or represents phenoxyphenyl, which can be substituted in one or two phenyl rings by halogen.

The naturally occurring pyrethroids (such as pyrethreum) are also particularly preferred carboxylic acid esters of the formula (III).

Examples which may be mentioned of the carboxylic acid esters of the formula (III) are: 2,2,2-trichloro-1-(3,4-dichloro-phenyl)-ethyl acetate, 3,4,5,6-tetrahydrophthalimido-methyl 2,2-dimethyl-3-(2-methyl-propen-1-yl)cyclopropane-carboxylate, 3-phenoxy-benzyl 2,2-dimethyl-3-(2,2-dichloro-vinyl)-cyclopropane-carboxylate, α-cyano-3-phenoxy-benzyl 2,2-dimethyl-3-(2,2-dichlorovinyl)cyclopropanecarboxylate, α-cyano-4-fluoro-3-phenoxybenzyl 2,2-dimethyl-3-(2,2-dichlorovinyl)-cyclopropanecarboxylate, pentafluorobenzyl 2,2-dimethyl-3-(2,2-dichlorovinyl)-cyclopropanecarboxylate, α-cyano-3-phenoxybenzyl 2,2-dimethyl-3-(2,2-dibromovinyl)-cyclopropanecarboxylate and α-cyano-3-phenoxy-benzyl 3-methyl-2-(4-chloro-phenyl)-butanoate.

The synergistic action of the compounds of the general formula (I) also preferentially manifests itself with (3) phosphoric acid esters and phosphonic acid esters of the general formula (IV)

in which the radicals X are identical or different and represent O or S,

Y represents O, S, —NH— of a direct bond between the central P atom and $R^{31}$, $R^{29}$ and $R^{30}$ are identical or different and represent alkyl or aryl, each of which is optionally substituted, and $R^{31}$ represents hydrogen, optionally substituted alkyl, aryl, heteroaryl, aralkyl, alkenyl, dioxanyl or an oxime radical, or represents the same radical to which it is bonded.

Particularly preferred phosphoric acid esters and phosphonic acid esters of the formula (IV) are those in which $R^{29}$ and $R^{30}$ are identical or different and represent $C_1$-$C_4$-alkyl or phenyl and $R^{31}$ represents hydrogen or alkyl which has 1 to 4 carbon atoms and is optionally substituted by halogen, hydroxyl, cyano, optionally halogen-substituted phenyl, carbamoyl, alkylsulphonyl, alkylsulphinyl, alkylcarbonyl, alkoxy, alkylthio, alkoxycarbonyl or alkylaminocarbonyl, the latter with in each case up to 6 carbon atoms, or represents alkenyl which has up to 4 carbon atoms and is optionally substituted by halogen, optionally halogen-substituted phenyl or $C_1$-$C_4$-alkoxycarbonyl, or represents the radical of the general formula

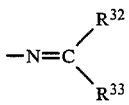

wherein $R^{32}$ and $R^{33}$ have the meaning given above for $R^{13}$ and, respectively, $R^{14}$, or represent cyano or phenyl, and in which $R^{31}$ furthermore represents dioxanyl, which is substituted by the same radical to which $R^{30}$ is bonded, or $R^{31}$ represents the same radical to which it is bonded, or $R^{31}$ represents phenyl, which is optionally substituted by methyl, nitro, cyano, halogen and/or methylthio, and wherein $R^{31}$ also particularly preferably represents a heteroaromatic radical, such as pyridinyl, quinolinyl, quinoxalinyl, pyrimidinyl or benzo-1,2,4-triazinyl, each of which is optionally substituted by $C_1$-$C_4$-alkoxy, $C_1$-$C_4$-alkylthiomethyl, $C_1$-$C_4$-alkyl and/or halogen.

Specific examples which may be mentioned are: O,O-dimethyl or O,O-diethyl O-(2,2-dichloro- or 2,2-dibromo-vinyl)phosphate, O,O-diethyl O-(4-nitrophenyl)thionophosphate, O,O-dimethyl O-(3-methyl-4-methylthiophenyl)thionophosphate, O,O-dimethyl O-(3-methyl-4-nitro-phenyl)thionophosphate, O-ethyl S-n-propyl O-(2,4-dichlorophenyl)thionophosphate, O-ethyl S-n-propyl O-(4-methylthio-phenyl)thionophosphate, O,O-dimethyl S-(4-oxo-1,2,3-benzotriazin-3-yl-methyl)thionothiolphosphate, O-methyl O-(2-iso-propyl-6-methoxy-pyrimidin-4-yl)thionomethanephosphonate, O,O-diethyl O-(2-iso-propyl-6-methyl-pyrimidin-4-yl)thionophosphate, O,O-diethyl O-(3-chloro-4-methyl-coumarin-7-yl)thionophosphate, O,O-dimethyl 2,2,2-trichloro-1-hydroxy-ethane-phosphonate and O,O-dimethyl S-(methylaminocarbonyl-methyl)thionophosphate.

The phosphorus-heterocyclic compounds which can be used according to the invention are characterized by the general formula (I).

The radicals shown in the formula (I) preferably have the following meaning:

The alkyl group in the alkylamino radical A is straight-chain or branched and contains 1 to 8, preferably 1 to 6 and in particular 1 to 4, carbon atoms. Examples which may be mentioned are methyl, ethyl and n- and i-propyl. Corresponding statements apply to the alkyl group in the N-alkyl-N-arylamino radical A.

The alkyl groups in the dialkylamino radical A and in the dialkylamino-alkyl radicals $R^1$ to $R^8$ are identical or different and are straight-chain or branched, and preferably contain 1 to 6, in particular 1 to 4, carbon atoms. Examples which may be mentioned are methyl, ethyl and n- and i-propyl.

In the dialkylamino-alkyl radicals $R^1$ to $R^8$, the alkyl groups to which the dialkylamino component is bonded preferably contain 1 to 6, in particular 1 to 4, carbon atoms.

The aryl group in N-alkyl-N-arylamino is preferably the phenyl group.

Optionally substituted alkyl A is straight-chain or branched alkyl with preferably 1 to 6, in particular 1 to 4, carbon atoms. Examples which may be mentioned are optionally substituted methyl, ethyl, n- and i-propyl and n-, i- and t-butyl.

Optionally substituted alkenyl or alkenyloxy A is straight-chain or branched alkenyl or alkenyloxy with preferably 2 to 6, in particular 2 to 4, carbon atoms. Examples which may be mentioned are optionally substituted ethenyl, prop-1-enyl, prop-2-enyl and but-3-enyl, propenyloxy and butenyloxy.

Optionally substituted alkoxy A is straight-chain or branched alkoxy with preferably 1 to 6, in particular 1 to 4, carbon atoms. Examples which may be mentioned are optionally substituted methoxy, ethoxy, n- and i-propoxy and n-, i- and t-butoxy.

Optionally substituted alkylthio A is straight-chain or branched alkylthio with preferably 1 to 6, in particular 1 to 4, carbon atoms. Examples which may be mentioned are optionally substituted methylthio, ethylthio, n- and i-propylthio and n-, i- and t-butylthio.

Optionally substituted aralkyl or aralkoxy A is aralkyl or aralkoxy which has preferably 6 or 10, in particular 6, carbon atoms in the aryl part and preferably 1 to 4, in particular 1 or 2, carbon atoms in the alkyl part and is optionally substituted in the aryl part and/or alkyl part, it being possible for the alkyl part to be straight-chain or branched. Examples which may be mentioned are optionally substituted benzyl, phenethyl, benzyloxy and phenethoxy.

In optionally halogen-substituted alkyl $R^1$ to $R^8$, alkyl denotes straight-chain or branched alkyl with preferably 1 to 6, in particular 1 to 4, carbon atoms. Examples which may be mentioned are methyl, ethyl, n- and i-propyl and n-, i- and t-butyl, each of which is optionally substituted by halogen, preferably fluorine, chlorine or bromine, and chloromethyl and bromomethyl being singled out in particular.

Optionally halogen-substituted alkenyl $R^1$ to $R^8$ is straight-chain or branched alkenyl with preferably 2 to 6, in particular 2 to 4, carbon atoms. Examples which may be mentioned are ethenyl, prop-1-enyl, prop-2-enyl and but-3-enyl, each of which is optionally substituted by halogen, preferably fluorine, chlorine or bromine.

The alkoxyalkyl and alkylthioalkyl radicals $R^1$ to $R^8$ which are optionally substituted by halogen (preferably fluorine, chlorine or bromine) preferably contain 2 to 8, in particular 2 to 6, carbon atoms.

Examples which may be mentioned are halogen-substituted methoxymethyl, ethoxymethyl, methoxymethyl, methylthiomethyl, methylthioethyl and ethylthiomethyl.

Two of the radicals $R^1$ to $R^8$, together with the carbon atom or atoms to which they are bonded, can form 5-membered to 7-membered cycloalkyl or cycloalkenyl rings, which can additionally be bridged by a methylene or ethylene group and which furthermore can be substituted by 1 or 2, preferably 1, alkyl group, preferably methyl or ethyl.

The optionally substituted radicals A and $R^1$ to $R^8$ can carry one or more, preferably 1 to 3 and in particular 1 or 2, identical or different substituents. Examples of substituents which may be listed are: alkyl with preferably 1 to 4, in particular 1 or 2, carbon atoms, such as methyl, ethyl, n- and i-propyl and n-, i- and t-butyl; alkoxy with preferably 1 to 4, in particular 1 or 2, carbon atoms, such as methoxy, ethoxy, n- and i-propoxy and n-, i- and t-butoxy; alkylthio with preferably 1 to 4, in particular 1 or 2, carbon atoms, such as methylthio, ethylthio, n- and i-propylthio and n- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl; halogen, preferably fluorine, chlorine, bromine and iodine, in particular chlorine and bromine;

cyano; nitro; alkylcarbonyl with preferably 2 to 5 carbon atoms and alkoxycarbonyl with preferably 2 to 5 carbon atoms.

Unless indicated otherwise, halogen in all cases denotes fluorine, chlorine, bromine and iodine, preferably fluorine, chlorine and bromine, in particular chlorine and bromine.

Preferably, in the compounds of the general formula (I), one of the indices n and m represents 0 and the other represents 0 or 1.

Compounds of the general formula (I) which are preferably used as synergists are those in which A represents amino, $C_1$–$C_4$-alkylamino, di-($C_1$–$C_4$-alkyl)-amino or N-phenyl-N-($C_1$–$C_4$-alkyl)-amino, or represents optionally halogen-substituted $C_1$–$C_4$-alkyl, $C_2$–$C_4$-alkenyl, $C_2$–$C_6$-alkenyloxy, $C_1$–$C_4$-alkoxy, phenyl, benzyl, benzyloxy or phenethoxy, or represents phenoxy, which can be substituted by a radical from the series comprising halogen, cyano, nitro, carbamoyl, $C_1$–$C_4$-alkylsulphonyl, $C_1$–$C_4$-alkylsulphinyl, $C_1$–$C_4$-alkylcarbonyl, $C_1$–$C_4$-alkyl, $C_1$–$C_4$-alkoxy, $C_1$–$C_4$-alkylthio and/or $C_1$–$C_4$-alkoxycarbonyl, $R^1$ to $R^8$ are identical or different and represent hydrogen, halogen, $NO_2$ or $C_1$–$C_6$-alkyl, which can be substituted by halogen, or $C_2$–$C_8$-alkenyl, di-($C_1$–$C_4$-alkyl)-amino, $C_1$–$C_4$-alkoxy-$C_1$–$C_4$-alkyl, $C_1$–$C_4$-alkylthio-$C_1$–$C_4$-alkyl, benzyl or phenyl, or in which two of the radicals $R^1$ to $R^8$, together with the carbon atom or atoms to which they are bonded, form a $C_5$–$C_7$-cycloalkyl or -cycloalkenyl ring, which can be substituted by methyl or ethyl and which can be bridged by a methylene or ethylene group to form a bicyclic ring, and n and m are identical or different and represent 0 or 1.

Compounds of the general formula (I) which are particularly preferably used as synergists are those in which A represents $C_1$–$C_4$-alkyl, $C_1$–$C_6$-alkoxy, $C_2$–$C_5$-alkenyloxy, $C_1$–$C_4$-alkylthio, $C_1$–$C_4$-alkylamino or di-($C_1$–$C_4$-alkyl)-amino, $R^1$ to $R^8$ are identical or different and represent hydrogen, nitro, optionally halogen-substituted $C_1$–$C_4$-alkyl or $C_1$–$C_4$-alkylthio-$C_1$–$C_4$-alkyl, or two of the radicals $R^1$ to $R^8$, together with the carbon atom or atoms to which they are bonded, form a 5-membered or 6-membered cycloalkyl or cycloalkenyl ring, which can be bridged by a methylene or ethylene group to form a bicyclic ring, and n and m are identical or different and represent 0 or 1.

Compounds of the general formula (I) which are very particularly preferred here are those in which A represents $C_1$–$C_4$-alkyl or $C_1$–$C_6$-alkoxy, $R^1$ to $R^8$ are identical or different and represent hydrogen or $C_1$–$C_4$-alkyl which is optionally substituted by chlorine or bromine and n and m are identical or different and represent 0 or 1, m preferably representing 0 or 1 and n preferably representing 0.

In respect of the meaning of n and m, the following preferred compounds of the general formula (I) result:

If n and m both denote 0, preferably A represents optionally halogen-substituted (preferably unsubstituted) $C_1$–$C_4$-alkyl, $R^1$ and $R^3$ represent hydrogen and p1 $R^2$ and $R^4$, which are identical or different, represent hydrogen or optionally halogen-substituted $C_1$–$C_6$-alkyl, or $R^2$ and $R^4$, together with the carbon atoms to which they are bonded, form a 5-membered or 6-membered cycloalkyl or cycloalkenyl ring which can be bridged by methylene or ethylene to form a bicyclic ring.

If m denotes 1 and n denotes 0, preferably A represents optionally halogen-substituted (preferably unsubstituted) $C_1$–$C_4$-alkyl, $R^1$, $R^2$, $R^5$ and $R^6$, which are identical or different, represent hydrogen or optionally halogen-substituted $C_1$–$C_6$-alkyl and $R^3$ and $R^4$, which are identical or different, represent hydrogen or optionally halogen-substituted $C_1$–$C_6$-alkyl, or $R^3$ and $R^4$, together with the carbon atom to which they are bonded, form a 5-membered or 6-membered cycloalkyl or cycloalkenyl ring, which can be bridged by a methylene or ethylene group to form a bicyclic ring.

If n and m denote 1, preferably A represents optionally halogen-substituted (preferably unsubtituted) $C_1$–$C_4$-alkyl and $R^1$ to $R^8$, which are identical or different, represent hydrogen or $C_1$–$C_6$-alkyl.

Particularly preferred compounds of the general formula (I) are the compounds in which A represents ethyl.

Those compounds in which at least one of the radicals $R^1$ or $R^2$ represents hydrogen and in which, if n denotes 0, at least one of the radicals $R^5$ and $R^6$ represents hydrogen, and in which, if n denotes 1, at least one of the radicals $R^7$ and $R^8$ represents hydrogen, are furthermore preferred. Most preferred are compounds of Examples 3, 4, 5, 7, 10 and 11.

The compounds of the general formula (I) are known or can be prepared by known methods and processes (compare, for example, Synth. React. Inorg. Met.-Org. Chem. 1976, 6 (2), 133–155 and U.S. Pat. No. 3,006,947).

The compounds of the formula (I) are accordingly obtained by a process in which the halides, which are known per se, of the general formula (V)

in which

Hal represents halogen, in particular chlorine, and

A has the abovementioned meaning, are reacted with compounds, which are known per se, of the formula VI

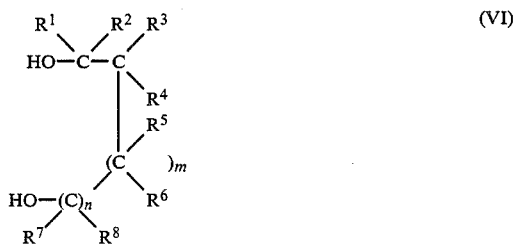

in which $R^1$ to $R^8$ and n and m have the abovementioned meaning, if appropriate in the presence of an acid acceptor, such as, for example, triethylamine or potassium carbonate, and if appropriate using a diluent, such as, for example, toluene or acetonitrile, at temperatures between 0° and 110° C. Working up is effected by customary methods, for example by extraction of the products with toluene from the reaction mixture, which has been diluted with water, washing the organic phase with water, drying and distillation or so-called "incipient distillation", that is to say by prolonged heating to moderately elevated temperatures under reduced pressure in order to free the products from the last volatile constituents.

The compounds are characterized by their refractive index, melting point, Rf value or boiling point.

The weight ratios of the synergists of the general formula (I) and active compounds (arthropodicides) can be varied within a relatively wide range. In general, the compounds of the formula (I) used as synergists are employed with the other active compounds in mixing ratios of between 1:100 and 100:1, preferably between 1:5 and 5:1 (parts by weight).

The active compound combinations according to the invention not only have a rapid knock-down action but also cause the destruction of animal pests, in particular insects and mites, which are encountered in agriculture, in forestry, in the protection of stored products and of materials and in the hygiene field. They are active against normally sensitive and resistant species and against all or some stages of development.

The animal pests which can be combated using the compounds of the formula (I) include, for example:

From the order of the Isopoda, for example, *Oniscus asellus* and *Porcellio scaber*. From the order of the Thysanura, for example, *Lepisma saccharina*. From the order of the Orthoptera, for example, *Blatta orientalis, Periplaneta americana, Leucophaea maderae, Blattella germanica, Acheta domesticus,* Gryllotalpa spp., *Locusta migratoria migratorioides* and *Schistocera gregaria*. From the order of the Dermaptera, for example, *Forficula auricularia*. From the order of the Isoptera, for example, Reticulitermes spp. From the order of the Anoplura, for example, *Pediculus humanus corporis,* Haematopinus spp. and Linograthus spp. From the order of the Mallophaga, for example, Trichodectes spp. and Damalinea spp. From the order of the Heteroptera, for example, *Cimex lectularius, Rhodnius prolixus* and Triatoma spp. From the order of the Homoptera, for example, Myzus spp. and Psylla spp. From the order of the Lepidoptera, for example, *Ephestia kuehniella* and *Galleria mellonella*. From the order of the Coleoptera, for example, *Anobium punctatum, Rhizopertha dominica, Bruchidius obtectus, Acanthoscelides obtectus, Hylotrupes bajulus, Oryzaephilus surinamensis,* Sitophilus spp., Dermestes spp., Trogoderma spp., Anthrenus spp., Attagenus spp., Lyctus spp., Ptinus spp., *Niptus hololeucus, Gibbium psylloides,* Tribolium spp. and *Tenebrio molitor*. From the order of the Hymenoptera, for example, Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocelphala,* Lycilia spp., Chrysomyia spp., Gastrophilus spp., Hyppobosca spp., Stomoxys spp., Oestrus spp., Hypderma spp. and Tabanus spp. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae,* Boophilus spp., Rhipicephalus spp., Amblyomma spp., Hyalomma spp., Ixodes spp., Psoroptes spp., Chorioptes spp. and Sarcoptes spp.

The active compound combinations of the compounds of the formula (I) and the other active compounds can be converted to the customary formulations, such as solutions, emulsions, wettable powders, suspensions, powders, dusts, foams, pastes, soluble powders, aerosols, suspension-emulsion concentrates, natural and synthetic materials impregnated with active compound, very fine capsules in polymeric substances and furthermore in formulations used with burning equipment, such as fumigating cartridges, fumigating cans, fumigating coils and the like, as well as ULV cold mist and warm mist formulations.

These formulations are produced in known manner, for example by mixing the mixtures of active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of watr as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexane, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers: ground natural minerals, such as kaolins, clays, talcs, chalk, quartz, attapulgite, montmorillonite or diatomaceous earth, and ground synthetic minerals, such as highly dispersed silicic acid, alumina and silicates; as solid carriers for granules: crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents: non-ionic and anionic emulsifiers, such as polyoxyethylene-fatty acid esters, polyoxyethylene-fatty alcohol ethers, for example alkylaryl polyglycol ethers and alkyl sulphonates; as dispersing agents: for example lignin and sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, buron, copper, cobalt, molybdenum and zinc.

The formulations in general contain between 0.1 and 95% by weight of active compound combination, preferably between 0.5 and 90%.

The active compound combinations according to the invention are used in the form of their commercially available formulations and/or in the use forms prepared from these formulations.

The total active compound content (including the synergist) of the use forms prepared from the commercially available formulations can vary within wide limits. The active compound concentration of the use forms can be from 0.001 to 95% by weight of active compound combination, preferably between 0.01 and 10% by weight.

The compounds are employed in a customary manner appropriate for the use forms.

When used against hygiene pests and pests of stored products, the active compound combinations are distinguished by an excellent residual action on wood and clay as well as a good stability to alkali on limed substrates.

The activity of the compounds of the formula (I) which can be used according to the invention may be illustrated by the following biological examples:

I Examples of active compounds which can be used according to the invention

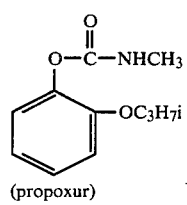
(propoxur)   (A)

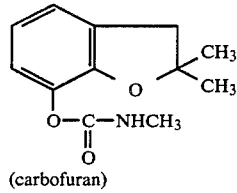
(carbofuran)   (B)

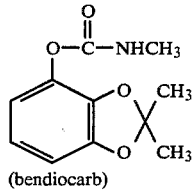
(bendiocarb)   (C)

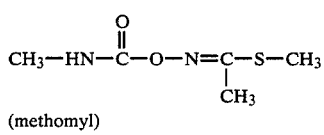
(methomyl)   (D)

(E) Pyrethrins of natural origin as a 25% strength extract

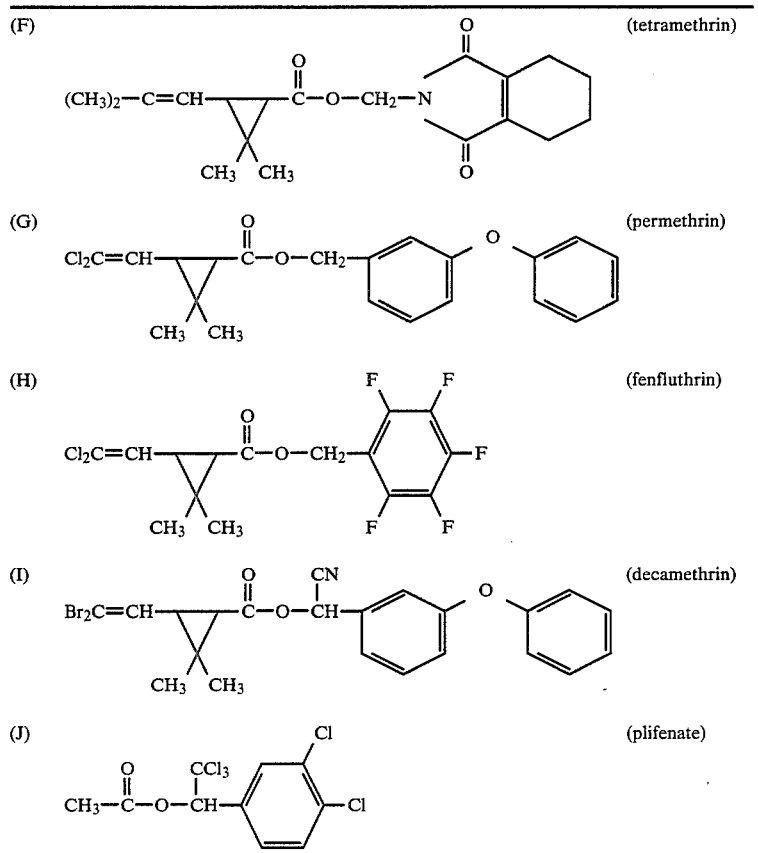

-continued

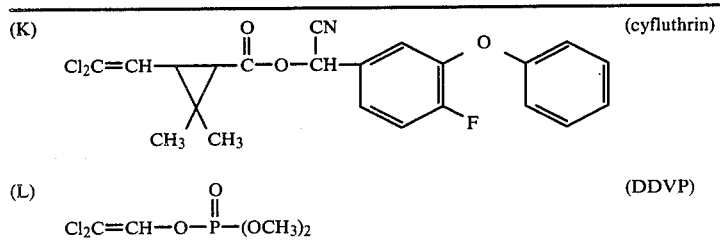

(K) (cyfluthrin)

(L) (DDVP)

II Examples of synergists which can be used according to the invention

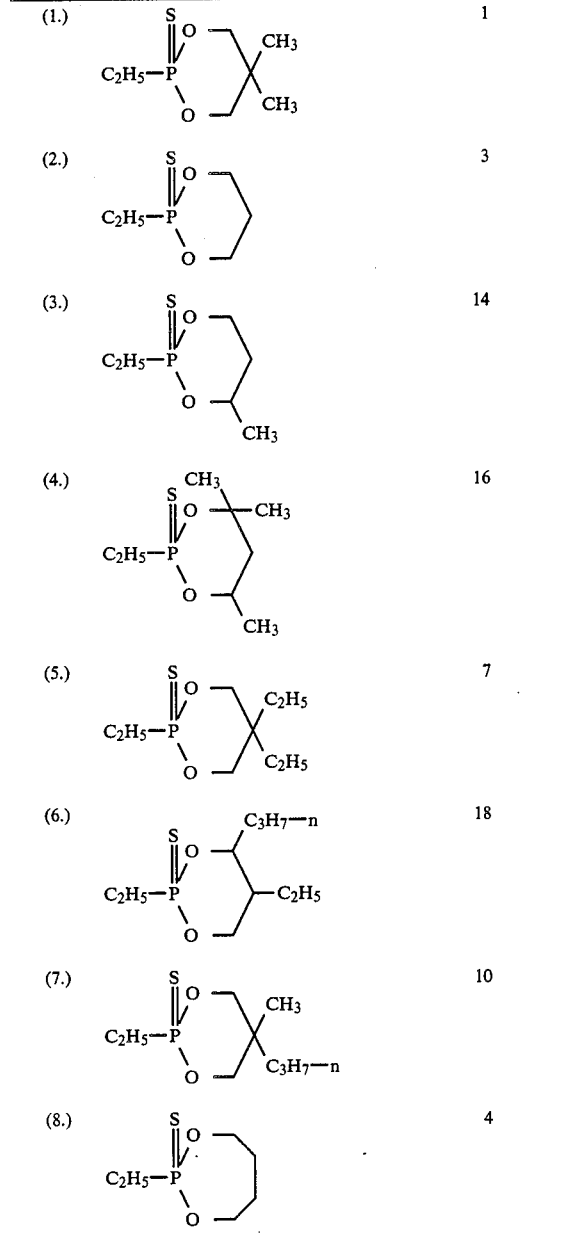

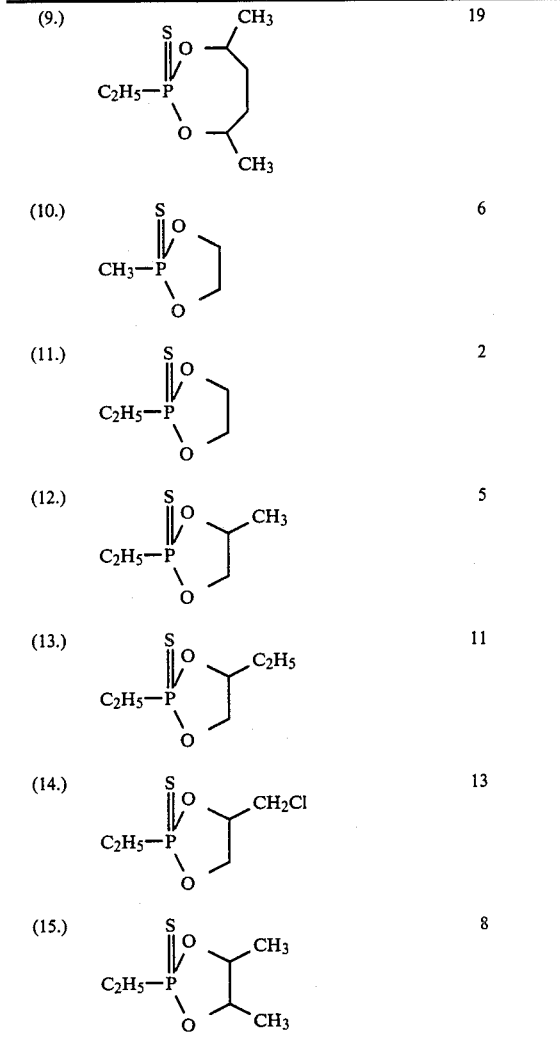

(d,l)

Synergist No. 7 is particularly preferred.

III Experimental procedure $KT_{100}$ test for synergists

Test insects: *Musca domestica*, Weymann's strain (resistant to carbamic acid esters and P esters)

Solvent: acetone

Solutions are prepared from the active compounds, synergists and mixtures of active compounds and synergists, and 2.5 ml of the solutions are pipetted onto filter-paper discs of 9.5 cm diameter in Petri dishes. The filter-paper absorbs the solutions. The Petri dishes are left standing open until the solvent has completely evaporated. 25 test insects are then introduced into the Petri dishes, and the dishes are covered with a glass lid.

The condition of the test insects is checked continuously for up to 6 hours. The time required for a 100% knock-down action is determined. If the $KT_{100}$ is not reached after 6 hours, the percentage of the insects which have been knocked down is determined.

The concentrations of the active compounds, synergists and mixtures and their actions, can be seen from the table which follows.

IV Experimental results

| Active compound Identifying Letter | + | Synergist No. | Active compound | + | Synergist | KT 100 in minutes or % after minutes |
|---|---|---|---|---|---|---|
| A | — | | 1.0 | — | | 360' = 15% |
| B | — | | 1.0 | — | | 360' = 25% |
| C | — | | 1.0 | — | | 360' = 10% |
| D | — | | 0.2 | — | | 360' = 95% |
| E | — | | 0.04 | — | | 360' = 70% |
| F | — | | 0.2 | — | | 150' |
| G | — | | 0.04 | — | | 105' |
| H | — | | 0.0016 | — | | 75' |
| I | — | | 0.008 | — | | 150' |
| J | — | | 1.0 | — | | 360' = 65% |
| K | — | | 0.008 | — | | 360' = 90% |
| L | — | | 0.008 | — | | 210' |
| — | | 1 | — | | 0.2 | 360' = 25% |
| — | | 2 | — | | 1.0 | 360' = 25% |
| — | | 3 | — | | 0.2 | 360' = 90% |
| — | | 4 | — | | 1.0 | 360' |
| — | | 5 | — | | 0.2 | 360' = 90% |
| — | | 6 | — | | 0.2 | 360' = 30% |
| — | | 7 | — | | 0.2 | 360' = 90% |
| — | | 8 | — | | 0.2 | 360' = 40% |
| — | | 9 | — | | 1.0 | 360' = 90% |
| — | | 10 | — | | 1.0 | 360' = 0% |
| — | | 11 | — | | 1.0 | 360' = 40% |
| — | | 12 | — | | 0.2 | 360' = 0% |
| — | | 13 | — | | 1.0 | 360' = 25% |
| — | | 14 | — | | 1.0 | 360' = 0% |
| — | | 15 | — | | 1.0 | 360' = 40% |
| — | | 16 | — | | 0.2 | 360' = 50% |
| — | | 17 | — | | 1.0 | 360' = 70% |
| — | | 18 | — | | 0.008 | 360' = 55% |
| — | | 19 (Standard) | — | | 1.0 | 360' = 0% |
| A | + | 1 | 0.008 | + | 0.008 | 150' |
| A | + | 2 | 0.008 | + | 0.008 | 180' |
| A | + | 3 | 0.04 | + | 0.04 | 75' |
| A | + | 4 | 0.04 | + | 0.04 | 60' |
| A | + | 5 | 0.008 | + | 0.008 | 120' |
| A | + | 6 | 0.04 | + | 0.04 | 120' |
| A | + | 7 | 0.04 | + | 0.04 | 75' |
| A | + | 8 | 0.008 | + | 0.008 | 180' |
| A | + | 9 | 0.04 | + | 0.04 | 90' |
| A | + | 10 | 0.04 | + | 0.04 | 150' |
| A | + | 11 | 0.04 | + | 0.04 | 120' |
| A | + | 12 | 0.04 | + | 0.04 | 90' |
| A | + | 13 | 0.008 | + | 0.008 | 180' |
| A | + | 14 | 0.04 | + | 0.04 | 90' |
| A | + | 15 | 0.008 | + | 0.008 | 150' |
| A | + | 16 | 0.04 | + | 0.04 | 75' |
| A | + | 17 | 0.04 | + | 0.04 | 90' |
| A | + | 18 | 0.008 | + | 0.008 | 105' |
| A | + | 19 | 0.2 | + | 0.2 | 360' = 90% |
| B | + | 1 | 0.008 | + | 0.008 | 210' |
| B | + | 2 | 0.008 | + | 0.008 | 150' |
| B | + | 3 | 0.04 | + | 0.04 | 120' |
| B | + | 4 | 0.04 | + | 0.04 | 150' |
| B | + | 5 | 0.008 | + | 0.008 | 210' |
| B | + | 6 | 0.04 | + | 0.04 | 105' |
| B | + | 7 | 0.008 | + | 0.008 | 210' |
| B | + | 8 | 0.04 | + | 0.04 | 105' |
| B | + | 9 | 0.04 | + | 0.04 | 180' |
| B | + | 10 | 0.2 | + | 0.2 | 150' |
| B | + | 11 | 0.2 | + | 0.2 | 120' |
| B | + | 12 | 0.04 | + | 0.04 | 105' |
| B | + | 13 | 0.008 | + | 0.008 | 150' |
| B | + | 14 | 0.04 | + | 0.04 | 150' |
| B | + | 15 | 0.008 | + | 0.008 | 210' |
| B | + | 16 | 0.008 | + | 0.008 | 180' |
| B | + | 17 | 0.04 | + | 0.04 | 150' |
| B | + | 18 | 0.008 | + | 0.008 | 180' |
| B | + | 19 | 1.0 | + | 1.0 | 360' = 75% |
| C | + | 1 | 0.04 | + | 0.04 | 90' |
| C | + | 2 | 0.04 | + | 0.04 | 150' |
| C | + | 3 | 0.04 | + | 0.04 | 180' |
| C | + | 4 | 0.04 | + | 0.04 | 105' |
| C | + | 5 | 0.008 | + | 0.008 | 180' |
| C | + | 6 | 0.04 | + | 0.04 | 105' |
| C | + | 7 | 0.04 | + | 0.04 | 90' |
| C | + | 8 | 0.04 | + | 0.04 | 120' |
| C | + | 9 | 0.04 | + | 0.04 | 180' |
| C | + | 11 | 0.2 | + | 0.2 | 150' |
| C | + | 12 | 0.04 | + | 0.04 | 150' |
| C | + | 13 | 0.04 | + | 0.04 | 90' |
| C | + | 14 | 0.04 | + | 0.04 | 150' |
| C | + | 15 | 0.04 | + | 0.04 | 150' |
| C | + | 16 | 0.008 | + | 0.008 | 180' |
| C | + | 17 | 0.04 | + | 0.04 | 150' |
| C | + | 18 | 0.008 | + | 0.008 | 120' |
| C | + | 19 | 0.2 | + | 0.2 | 360' = 85% |
| D | + | 1 | 0.2 | + | 0.2 | 75' |
| D | + | 2 | 0.2 | + | 0.2 | 90' |
| D | + | 3 | 0.2 | + | 0.2 | 90' |
| D | + | 4 | 0.2 | + | 0.2 | 90' |
| D | + | 5 | 0.04 | + | 0.04 | 120' |
| D | + | 6 | 0.2 | + | 0.2 | 60' |
| D | + | 7 | 0.2 | + | 0.2 | 75' |
| D | + | 8 | 0.2 | + | 0.2 | 105' |
| D | + | 9 | 0.2 | + | 0.2 | 120' |
| D | + | 11 | 0.2 | + | 0.2 | 105' |
| D | + | 12 | 0.2 | + | 0.2 | 105' |
| D | + | 13 | 0.2 | + | 0.2 | 75' |
| D | + | 14 | 0.2 | + | 0.2 | 75' |
| D | + | 15 | 0.04 | + | 0.04 | 120' |
| D | + | 16 | 0.2 | + | 0.2 | 75' |
| D | + | 17 | 0.2 | + | 0.2 | 75' |
| D | + | 19 | 0.2 | + | 0.2 | 150' |
| E | + | 5 | 0.04 | + | 0.04 | 60' |
| E | + | 6 | 0.04 | + | 0.04 | 60' |
| E | + | 7 | 0.04 | + | 0.04 | 60' |
| E | + | 13 | 0.04 | + | 0.04 | 60' |
| E | + | 19 | 0.04 | + | 0.04 | 90' |
| F | + | 1 | 0.2 | + | 0.2 | 45' |
| F | + | 2 | 0.2 | + | 0.2 | 30' |
| F | + | 3 | 0.2 | + | 0.2 | 30' |
| F | + | 4 | 0.2 | + | 0.2 | 30' |
| F | + | 5 | 0.2 | + | 0.2 | 30' |
| F | + | 6 | 0.2 | + | 0.2 | 30' |
| F | + | 7 | 0.2 | + | 0.2 | 30' |
| F | + | 8 | 0.2 | + | 0.2 | 30' |
| F | + | 9 | 0.2 | + | 0.2 | 45' |
| F | + | 12 | 0.2 | + | 0.2 | 45' |
| F | + | 13 | 0.2 | + | 0.2 | 45' |
| F | + | 14 | 0.2 | + | 0.2 | 30' |
| F | + | 15 | 0.2 | + | 0.2 | 30' |
| F | + | 17 | 0.2 | + | 0.2 | 30' |
| F | + | 19 | 0.2 | + | 0.2 | 60' |
| G | + | 4 | 0.04 | + | 0.04 | 75' |
| G | + | 5 | 0.04 | + | 0.04 | 45' |
| G | + | 12 | 0.04 | + | 0.04 | 75' |
| G | + | 16 | 0.04 | + | 0.04 | 75' |
| G | + | 17 | 0.04 | + | 0.04 | 75' |
| G | + | 19 | 0.04 | + | 0.04 | 90' |
| H | + | 2 | 0.0016 | + | 0.0016 | 45' |
| H | + | 18 | 0.0016 | + | 0.0016 | 45' |
| H | + | 19 | 0.0016 | + | 0.0016 | 60' |

-continued

IV Experimental results

| Active compound Identifying Letter | + | Synergist No. | Concentrations in % Active compound | + | Synergist | KT 100 in minutes or % after minutes |
|---|---|---|---|---|---|---|
| I | + | 3 | 0.008 | + | 0.008 | 90' |
| I | + | 7 | 0.008 | + | 0.008 | 90' |
| I | + | 13 | 0.008 | + | 0.008 | 90' |
| I | + | 17 | 0.008 | + | 0.008 | 90' |
| I | + | 19 | 0.008 | + | 0.008 | 105' |
| J | + | 1 | 0.04 | + | 0.04 | 180' |
| J | + | 11 | 0.04 | + | 0.04 | 240' |
| J | + | 19 | 0.2 | + | 0.2 | 360' = 55% |
| K | + | 2 | 0.008 | + | 0.008 | 120' |
| K | + | 3 | 0.008 | + | 0.008 | 105' |
| K | + | 4 | 0.008 | + | 0.008 | 105' |
| K | + | 6 | 0.008 | + | 0.008 | 120' |
| K | + | 7 | 0.008 | + | 0.008 | 120' |
| K | + | 8 | 0.008 | + | 0.008 | 120' |
| K | + | 13 | 0.008 | + | 0.008 | 105' |
| K | + | 16 | 0.008 | + | 0.008 | 120' |
| K | + | 18 | 0.008 | + | 0.008 | 120' |
| K | + | 19 | 0.008 | + | 0.008 | 150' |
| L | + | 1 | 0.008 | + | 0.008 | 120' |
| L | + | 2 | 0.008 | + | 0.008 | 150' |
| L | + | 3 | 0.008 | + | 0.008 | 120' |
| L | + | 6 | 0.008 | + | 0.008 | 150' |
| L | + | 7 | 0.008 | + | 0.008 | 150' |
| L | + | 15 | 0.008 | + | 0.008 | 150' |
| L | + | 18 | 0.008 | + | 0.008 | 75' |
| L | + | 19 | 0.008 | + | 0.008 | 360' = 95% |

The preparation of the synergists which can be used according to the invention may be illustrated with the aid of the following examples:

EXAMPLE 1

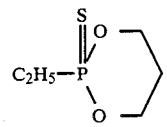

1. 2-Ethyl-5,5-dimethyl-1,3,2-dioxophosphorinane 2-sulphide

A mixture of 20 g (0.2 mole) of neopentylglycol and 40.4 g (0.4 mole) of triethylamine in 300 ml of methylene chloride is added to 32.6 g (0.2 mole) of ethanethiophosphonic acid dichloride, dissolved in 300 ml of toluene, at 20° C. in the course of 3 hours. The mixture is stirred at 20° C. for 12 hours, the solid is filtered off, the filtrate is dried over magnesium sulphate, the solvent is distilled off under a waterpump vacuum and volatile constituents are removed in an oil pump vacuum (50° C. bath/0.1 mbar). For further purification, the product is taken up again in methylene chloride, the mixture is filtered with suction over silica gel and the product is freed from volatile constituents as described above. 20.4 g (53% of theory) of 2-ethyl-5,5-dimethyl-1,3,2-dioxophosphorinane-2-sulphide with a refractive index $n_D^{20}$ of 1.5042 are obtained as the residue.

The following compounds can be obtained analogously (in the case of the boiling points, the pressure is given in mbar):

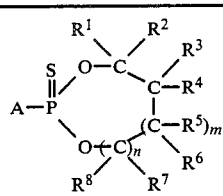

(I)

| Example No. | A | n | m | R¹ | R² | R³ | R⁴ | R⁵ | R⁶ | R⁷ | R⁸ | Physical data |
|---|---|---|---|---|---|---|---|---|---|---|---|---|
| 2 | C₂H₅ | 0 | 0 | H | H | H | H | — | — | — | — | $n_D^{20}$ = 1.5218 |
| 3 | " | 0 | 1 | " | " | " | " | H | H | — | — | $n_D^{20}$ = 1.5101 |
| 4 | " | 1 | 1 | " | " | " | " | " | " | H | H | $n_D^{20}$ = 1.5227 |
| 5 | " | 0 | 0 | CH₃ | " | " | " | — | — | — | — | $n_D^{20}$ = 1.5291 |
| 6 | CH₃ | 0 | 0 | H | " | " | " | — | — | — | — | Melting point 75° C. |
| 7 | C₂H₅ | 0 | 1 | H | H | C₂H₅ | C₂H₅ | H | H | — | — | $n_D^{20}$ = 1.5041; Melting point 38° C. |
| 8 | " | 0 | 0 | CH₃ | H (dl) - mixture | CH₃ | H | — | — | — | — | $n_D^{20}$ = 1.4994 |
| 9 | " | 0 | 0 | CH₃ | H (meso) | CH₃ | H | — | — | — | — | $n_D^{20}$ = 1.5147 |
| 10 | " | 0 | 1 | H | H | CH₃ | n-C₃H₇ | H | H | — | — | $n_D^{20}$ = 1.4985 |
| 11 | " | 0 | 0 | C₂H₅ | H | H | H | — | — | — | — | $n_D^{20}$ = 1.5112 |
| 12 | (CH₃)₃CCH₂NH | 0 | 0 | H | H | H | H | — | — | — | — | Rf.(Hexane:Acetone = 7:3) 0.614 |
| 13 | C₂H₅ | 0 | 0 | CH₂Cl | " | " | " | — | — | — | — | $n_D^{20}$ = 1.5286 |
| 14 | " | 0 | 1 | CH₃ | " | " | " | H | H | — | — | $n_D^{20}$ = 1.5039 |
| 15 | (CH₃)₃CCH₂O | 0 | 0 | H | H | H | H | — | — | — | — | $n_D^{20}$ = 1.4782 |
| 16 | C₂H₅ | 0 | 1 | CH₃ | CH₃ | H | H | CH₃ | H | — | — | $n_D^{20}$ = 1.5019 |
| 17 | (CH₃)₂CHO | 0 | 0 | H | H | H | H | — | — | — | — | Rf. (Hex:Ac = 7:3) 0.659 |
| 18 | C₂H₅ | 0 | 1 | n-C₃H₇ | H | CH₃CH₂ | H | H | H | — | — | $n_D^{20}$ = 1.4988 |
| 19 | " | 1 | 1 | CH₃ | H | H | H | H | H | CH₃ | H | $n_D^{20}$ = 1.5199 |

-continued

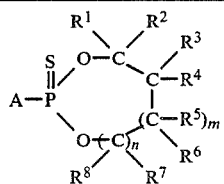
(I)

| Example No. | A | n | m | $R^1$ | $R^2$ | $R^3$ | $R^4$ | $R^5$ | $R^6$ | $R^7$ | $R^8$ | Physical data |
|---|---|---|---|---|---|---|---|---|---|---|---|---|
| 20 | " | 0 | 1 | $CH(CH_3)_2$ | H | $CH_3$ | $CH_3$ | " | " | — | — | |
| 21 | " | 0 | 1 | H | H | $-CH_2-C\equiv C-CH_2-CH_2-$ H, $CH_3$ | | " | " | — | — | |
| 22 | $n-C_4H_9$ | 0 | 1 | " | " | $n-C_3H_7$ | $CH_3$ | " | " | — | — | |
| 23 | $C_2H_5$ | 0 | 1 | " | " | (cyclohexenyl-$CH_2$) | | " | " | — | — | |
| 24 | $C_2H_5$ | 0 | 1 | H | H | $-CH_2-CH=CH-(CH_2)_2-$ | | H | H | — | — | |
| 25 | $n-C_3H_7$ | 0 | 1 | " | " | $n-C_3H_7$ | $CH_3$ | " | " | — | — | $n_D^{20} = 1.500$ |
| 26 | $C_2H_5$ | 0 | 0 | $n-C_3H_7$ | " | H | H | — | — | — | — | |
| 27 | " | 0 | 0 | $n-C_4H_9$ | " | " | " | — | — | — | — | $n_D^{20} = 1.496$ |
| 28 | " | 0 | 0 | $n-C_6H_{13}$ | " | " | " | — | — | — | — | $n_D^{20} = 1.485$ |
| 29 | " | 0 | 0 | H | $-CH_2(CH_2)_2-$ $-CH_2-$ (trans) | | " | — | — | — | — | Melting point 107° C. |
| 30 | " | 0 | 1 | H | H | $-CH_2(CH_2)_2CH_2-$ | | H | H | — | — | Melting point 48° C. |
| 31 | " | 0 | 0 | $CH_2S-$ $-C_2H_5$ | " | H | H | — | — | — | — | $n_D^{20} = 1.539$ |
| 32 | $SC_3H_7-n$ | 0 | 1 | H | H | $C_2H_5$ | $C_2H_5$ | H | H | — | — | Melting point 43° C. |
| 33 | $CH_3$ | 0 | 1 | H | $CH_3$ | $CH_3$ | $CH_3$ | H | $CH_3$ | — | — | |
| 34 | $CH_3$ | 0 | 1 | H | H | $C_2H_5$ | $C_2H_5$ | H | H | — | — | Melting point 61° C. |
| 35 | $SC_3H_7-n$ | 0 | 1 | H | H | $CH_3$ | $CH_3$ | H | H | — | — | Melting point 37° C. |
| 36 | $CH_3$ | 0 | 1 | H | $CH_3$ | H | $CH_3$ | H | $CH_3$ | — | — | |
| 37 | $CH_3$ | 0 | 1 | H | $CH_3$ | H | H | H | H | — | — | |
| 38 | $CH_3$ | 0 | 1 | H | H | $NO_2$ | $CH_3$ | H | H | — | — | Melting point 108° C. |
| 39 | $CH_3$ | 0 | 1 | H | H | $NO_2$ | $C_2H_5$ | H | H | — | — | Melting point 104° C. |
| 40 | $NHCH_3$ | 0 | 1 | H | H | $C_2H_5$ | $C_2H_5$ | H | H | — | — | Melting point 94° C. |
| 41 | $CH_3$ | 0 | 1 | $CH_3$ | $CH_3$ | H | H | $CH_3$ | H | — | — | |
| 42 | $CH_3$ | 0 | 1 | H | H | $ClCH_2$ | $C_2H_5$ | H | H | — | — | Melting point 86° C. |
| 43 | $NHC_3H_7i$ | 0 | 1 | H | H | $C_2H_5$ | $C_2H_5$ | H | H | — | — | Melting point 53–55° C. |
| 44 | $CH_3$ | 0 | 1 | H | H | $CH_3$ | $CH_3$ | H | H | — | — | Melting point 63° C. |
| 45 | $CH_3$ | 0 | 1 | H | H | $CH_3$ | $n-C_3H_7$ | H | H | — | — | |
| 46 | $CH_3$ | 0 | 1 | H | $i-C_3H_7$ | $CH_3$ | $CH_3$ | H | H | — | — | Melting point 58° C. |
| 47 | $CH_3$ | 0 | 1 | H | H | H | H | H | H | — | — | Melting point 82–83° C. |
| 48 | $C_2H_5$ | 0 | 1 | H | $CH_3$ | H | $CH_3$ | H | $CH_3$ | — | — | |
| 49 | $CH_3$ | 0 | 1 | H | H | H | $C_2H_5$ | H | $n-C_3H_7$ | — | — | |
| 50 | $CH_3$ | 0 | 1 | H | H | $C_2H_5$ | $n-C_4H_9$ | H | H | — | — | |
| 51 | $CH_3$ | 0 | 0 | H | H | H | $CH_3$ | — | — | — | — | |
| 52 | $CH_3$ | 0 | 0 | H | $CH_3$ | H | $CH_3$ | — | — | — | — | |
| 53 | $C_2H_5$ | 0 | 1 | H | $CH_3$ | $CH_3$ | $CH_3$ | H | $CH_3$ | — | — | |
| 54 | $N(CH_3)_2$ | 0 | 1 | H | H | $CH_3$ | $n-C_3H_7$ | H | H | — | — | Boiling point 0.01 96° C. |
| 55 | $N(C_2H_5)_2$ | 0 | 1 | H | H | $CH_3$ | $CH_3$ | H | H | — | — | Melting point 61° C. |
| 56 | $N(CH_3)_2$ | 0 | 1 | H | H | $C_2H_5$ | $C_2H_5$ | H | H | — | — | Melting point 51° C. |
| 57 | $N(CH_3)_2$ | 0 | 1 | H | H | $CH_3$ | $n-C_3H_7$ | H | H | — | — | Melting point 91–95° C. |
| 58 | $SC_2H_5$ | 0 | 0 | H | $CH_3$ | H | $CH_3$ | — | — | — | — | Boiling point |

-continued

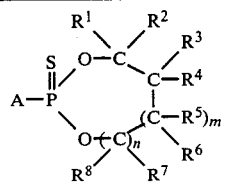
(I)

| Example No. | A | n | m | $R^1$ | $R^2$ | $R^3$ | $R^4$ | $R^5$ | $R^6$ | $R^7$ | $R^8$ | Physical data |
|---|---|---|---|---|---|---|---|---|---|---|---|---|
| 59 | $SC_2H_5$ | 0 | 1 | H | H | $C_2H_5$ | $C_2H_5$ | H | H | — | — | 0.07 84° C. |
| 60 | $N(CH_3)_2$ | 0 | 0 | H | $CH_3$ | H | $CH_3$ | — | — | — | — | Boiling point 0.01 86° C. |
| 61 | $N(C_2H_5)_2$ | 0 | 0 | H | $CH_3$ | H | $CH_3$ | — | — | — | — | Boiling point 0.01 92° C. |
| 62 | $OCH_3$ | 0 | 1 | H | H | $CH_3$ | $CH_3$ | H | H | — | — | Melting point 92° C. |
| 63 | $N(C_2H_5)_2$ | 0 | 0 | H | H | H | H | — | — | — | — | Boiling point 0.01 90° C. |
| 64 | $SC_2H_5$ | 0 | 0 | H | $CH_3$ | H | H | — | — | — | — | Boiling point 0.01 88° C. |
| 65 | $N(CH_3)_2$ | 0 | 0 | H | H | H | H | — | — | — | — | Boiling point 0.01 84° C. |
| 66 | $SC_2H_5$ | 0 | 0 | H | H | H | H | — | — | — | — | Boiling point 0.01 73° C. |
| 67 | $N(C_2H_5)_2$ | 0 | 0 | H | H | H | $CH_3$ | — | — | — | — | Boiling point 0.01 91° C. |
| 68 | $CH_3$ | 0 | 1 | H | H | $BrCH_2$ | $BrCH_2$ | H | H | — | — | |
| 69 | $OCH_2CH=CH_2$ | 0 | 1 | H | H | $CH_3$ | $CH_3$ | H | H | — | — | |
| 70 | $OCH_2CH=C\genfrac{}{}{0pt}{}{CH_3}{CH_3}$ | 0 | 1 | H | H | $CH_3$ | $CH_3$ | H | H | — | — | |
| 71 | $C_2H_5$ | 0 | 1 | H | H | $C_2H_5$ | $C_4H_9-n$ | H | H | — | — | $n_D^{20} = 1.5009$ |

It is understood that the specification and examples are illustrative but not limitative of the present invention and that other embodiments within the spirit and scope of the invention will suggest themselves to those skilled in the are.

We claim:

1. An arthropodicidal composition comprising an arthropodicidally effective amount of (A) an arthropodicidally active compound selected from the group consisting of arthropodicidally active carbamic acid esters, carboxylic acid esters, phosphoric acid esters and phosphonic acid esters and (B) a synergist compound of the formula

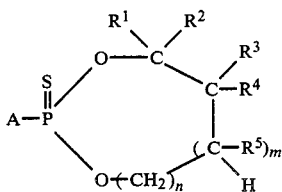

in which
A is $C_1$–$C_4$-alkyl or $C_1$–$C_6$-alkoxy,
$R^1$ is hydrogen, $C_1$–$C_4$-alkyl or halogen-substituted $C_1$–$C_4$-alkyl,
$R^2$, $R^3$, $R^4$ and $R^5$ each independently is hydrogen or $C_1$–$C_4$-alkyl, and
n and m each independently is 0 or 1 wherein the ratio of A to B is 1:5 to 5:1.

2. A composition according to claim 1, wherein the arthropodicidally active compound is a carbamic acid ester.

3. A composition according to claim 1, wherein the synergist is

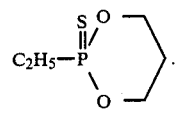

4. A composition according to claim 1, wherein the synergist is

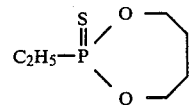

5. A composition according to claim 1, wherein the synergist is

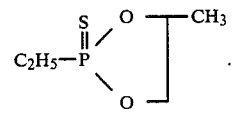

6. A composition according to claim 1, wherein the synergist is

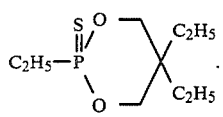

7. A composition according to claim 1, wherein the synergist is

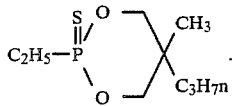

8. A composition according to claim 1, wherein the synergist is

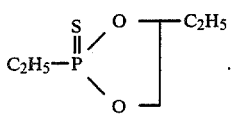

9. A method of combating arthropods which comprises applying to arthropods or to a habitat thereof an arthropodicidally effective amount of a composition according to claim 1.

10. The method according to claim 9, wherein the synergist of the composition is selected from the group consisting of

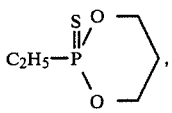

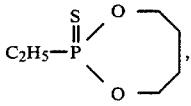

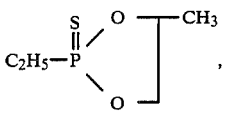

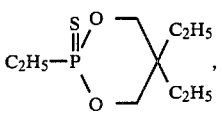

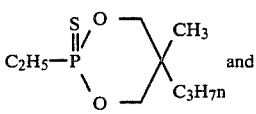

and

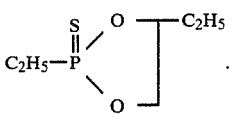

* * * * *

UNITED STATES PATENT AND TRADEMARK OFFICE
CERTIFICATE OF CORRECTION

PATENT NO. : 4,678,777     Page 1 of 2
DATED : July 7, 1987
INVENTOR(S) : Krüger et al.

It is certified that error appears in the above-identified patent and that said Letters Patent is hereby corrected as shown below:

| | |
|---|---|
| Col. 5, line 47 | Delete rightside of middle and last structure and substitute: 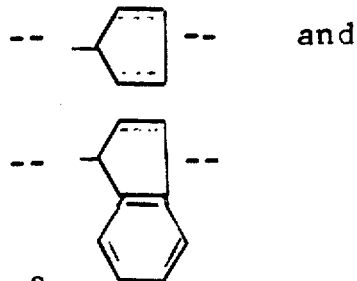 |
| Col. 9, line 67 | Before "$R^2$" delete "$pl_2^"$ and start new paragraph with "$R^2$" |
| Col. 10, line 23 | Correct spelling of --unsubstituted-- |
| Col. 11, line 62 | Correct spelling of --erythrocephala-- and --Lucilia-- |
| Col. 12, line 24 | Correct spelling of --water-- |
| Col. 12, line 35 | Delete "cyclohexane" and substitute --cyclohexanone-- |
| Col. 12, line 68 | Delete "buron" and substitute --boron-- |
| Col. 16, line 58 | Insert: 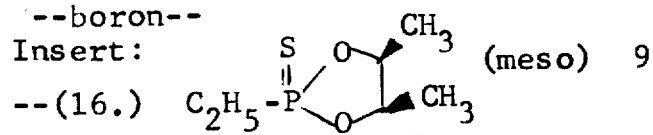 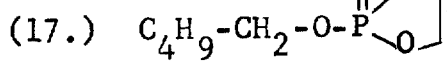 |

UNITED STATES PATENT AND TRADEMARK OFFICE
CERTIFICATE OF CORRECTION

PATENT NO. : 4,678,777           Page 2 of 2

DATED     : July 7, 1987

INVENTOR(S) : Bernd-Wieland Krüger, et al.

It is certified that error appears in the above-identified patent and that said Letters Patent is hereby corrected as shown below:

(18.) Piperonyl butoxide (known) as a standard--

Col. 20, line 7    End of formula insert -- as follows   $\diagup^{CH_3}_{\diagdown CH_3}$ --

Col. 21, Example 21, 2nd line under "R³"    Under "C=C" insert -- ∼ --

Signed and Sealed this

Fifth Day of April, 1988

Attest:

DONALD J. QUIGG

Attesting Officer    Commissioner of Patents and Trademarks